United States Patent [19]

Glabiszewski

[11] Patent Number: 4,513,457

[45] Date of Patent: Apr. 30, 1985

[54] ARTICULATED HIP-JOINT FOR AN ARTIFICIAL LEG

[75] Inventor: Richard Glabiszewski, Duderstadt, Fed. Rep. of Germany

[73] Assignee: Otto Bock Orthopädische Industrie KG, Duderstadt, Fed. Rep. of Germany

[21] Appl. No.: 486,848

[22] Filed: Apr. 20, 1983

[30] Foreign Application Priority Data

Apr. 21, 1982 [DE] Fed. Rep. of Germany ....... 3214773

[51] Int. Cl.³ .............................. A61F 1/08; A61F 1/04
[52] U.S. Cl. ................................................ 3/15; 3/21
[58] Field of Search ................................. 3/2, 14–16, 3/17 R, 21

[56] References Cited

U.S. PATENT DOCUMENTS 4,051,558 10/1977 Vallotton ........................... 3/15 X
4,215,441 8/1980 Wilson .............................. 3/15

FOREIGN PATENT DOCUMENTS 735844 5/1943 Fed. Rep. of Germany ........... 3/2
2754384 6/1978 Fed. Rep. of Germany .......... 3/15

OTHER PUBLICATIONS

"The IPOS Hip Joint for Hip Disarticulation or Hemipelvectomy Prostheses", Hosmer Dorrance Corp., P.O. Box 37, Campbell, California 95008, (4 pages), received Jun. 23, 1978, 3–15.

Primary Examiner—Ronald L. Frinks
Attorney, Agent, or Firm—Michael J. Striker

[57] ABSTRACT

In a prosthetic hip-joint for an artificial leg a first joint member is connected to an upright shank of a two-shank fastening angle. A second joint member is pivotally connected to the first joint member by a pivot so that the second member can be pivoted relative to the first member between a first position corresponding to the standing position of the leg and a second position corresponding to the sitting position of the leg. The joint further includes stop surface abutments on the first member and the second member for limiting the pivoting movement of the second member relative to the first member and a compression spring on the second member for generating an elastic counter force applied to second member when it is pivoted from the first position into the second position and vice versa such that in the sitting position the first and second members do not extend downwardly from a horizontal shank of the fastening angle.

13 Claims, 7 Drawing Figures

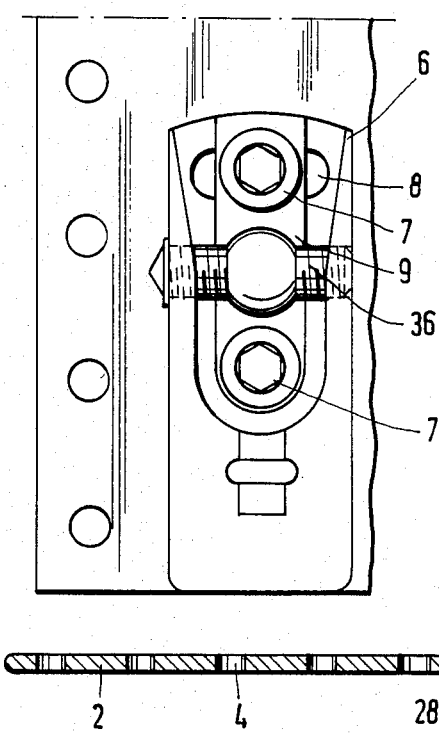
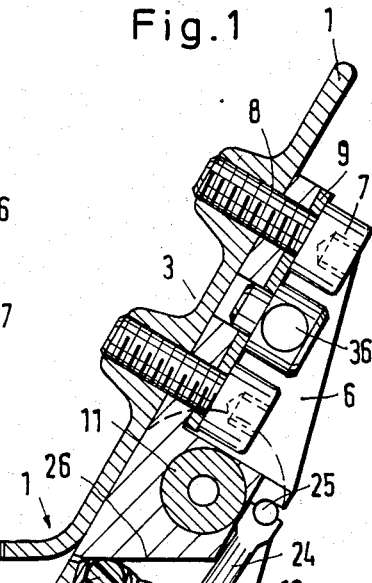
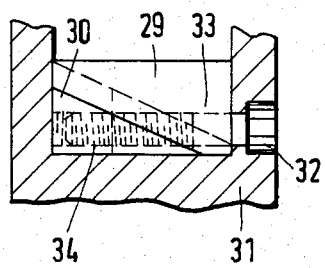
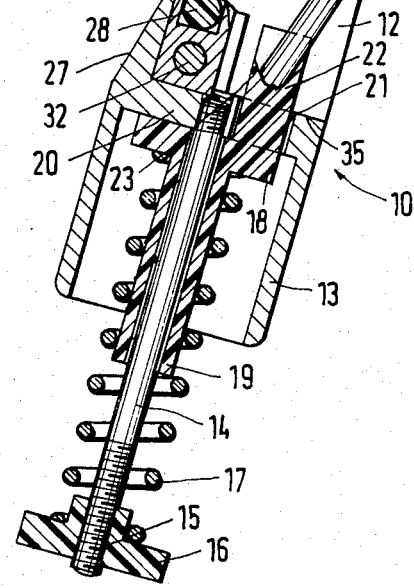
Fig. 4
Fig. 1
Fig. 3

ARTICULATED HIP-JOINT FOR AN ARTIFICIAL LEG

BACKGROUND OF THE INVENTION

The invention relates generally to articulated joints used for prosthetic devices. More particularly, the invention relates to hip-joints for artificial legs.

Known hip-joints of the type under discussion include a fastening angle to be secured to a support on a human body and having a substantially horizontal shank and a substantially upright shank carrying the joint which is comprised of two joint members one of which is pivotable relative to the other so that the joint can take a position corresponding to the standing position of the artificial leg or a position corresponding to the sitting position of the artificial leg.

The above described hip-joints have been known and used for many years when it has been necessary to use a totally artificial leg. The fastening angle is usually connected to the support strapped about the base of the amputated leg. An elastic means between the first joint member and the second joint member has been usually employed in order to hold the artificial leg in the standing and sitting positions and provide for an optimal movement of the artificial upper shank.

The first joint element is usually applied to the substantially horizontal shank of the fastening angle in known hip-joint structures. The elastic means between the first joint member and the second joint member have been formed as elastic bands or strips which have been clamped between both joint members or between one of the members and the artificial leg.

Conventional prosthetic hip-joints have required relatively large space. This has caused certain cosmetic difficulties, particularly in the sitting position of a prosthesis carrier. The problem occurred because with conventional hip-joints in the sitting position of the user the joint is merely pushed out from the seat surface so that a comfortable sitting position is badly disturbed. Furthermore, conventional hip-joints are not optimal in handling.

There has been also known a prosthetic hip-joint provided with a lock which, however permits for only a very limited movement of the hip-joint during walking. Furthermore, a prosthesis carrier should have manually loosened the lock in order to take a sitting position. The lock had a locking function for the standing position. Such conventional hip-joints are not comparable with the hip-joints described herein above because they cause inconveniences for a user in that the manually operated lock must be always accessible. Furthermore, the function of the lock can be carried out in relatively new hip-joints by elastic bands.

SUMMARY OF THE INVENTION

It is an object of the invention to provide an improved articulated hip-joint.

It is a further object of the invention to provide a prosthetic hip-joint which is easy to handle and which is comfortable for a user.

It is another object of the invention to provide an articulated hip-joint with satisfactory cosmetic appearance.

These and other objects of the invention are attained by an articulated hip-joint for an artificial leg, comprising a fastening angle including a substantially horizontal shank and a substantially upright shank extended at an obtuse angle to said horizontal shank; a first joint member connected to said upright shank; a second joint member connectable to the artificial leg and pivotally connected to said first joint member by a pivot so that said second member can be pivoted relative to said first member about said pivot between a first position corresponding to the standing position of the leg and a second position corresponding to the sitting position of the leg; stop surface means on said first member and said second member for limiting the pivoting movement of said second member relative to said first member; and elastic means on said second member for generating an elastic counter force applied to said second member when it is pivoted from said first position into said second position and vice versa so that said first joint member and said second joint member do not extend downwardly over an imaginary extension line drawn from said substantially horizontal shank when the joint is in said second position.

The main advantage of the articulated hip-joint according to the invention is that a user is not disturbed in his or her sitting position because the overall height of the joint is zero in the downward direction in that sitting position. Thus the prosthetic hip-joint of the invention is compact and has nice cosmetic appearance.

According to a further feature of the invention it may include means for connecting the first member to said upright shank operated so that said first member is pivotable at a small angle relative to the upright shank in a vertical plane.

This connecting means may include two openings formed in said first member in spaced relationship from each other and two fastening screws extended through said openings, respectively and received in said upright shank, one of said openings being a circular oblong opening. Such a construction makes it possible that the artificial leg can be adjusted in the saggital plane. Although such an adjustment is also possible with conventional prosthetic hip-joints the hip-joint according to the invention ensures an adjustment of the prosthesis to individual qualities of a user without, however, modifying the leg prosthesis itself. The above mentioned oblong opening renders possible a pivoting movement of the first joint member about a horizontal axis which is perpendicular to the upright shank of the fastening angle.

In addition to an adjustment in the saggital plane the joint according to the invention allows for an adjustment in the frontal plane. This is obtained by the aforementioned stop surface means which may include a lower side of said first member and an upper side of the second member, said upper side striking against said lower side when the joint is in said first position.

According to a still further feature of the invention the hip-joint may include means for adjusting the position of said upper side at the height thereof. Due to this adjusting means an angle of the upper shank of the artificial leg in its standing position can be adjusted.

This adjusting means may include a wedge-like support element having a sloped surface and a wedge-like counter element having an inclined surface, said sloped surface being supported on said inclined surface, the relative position of said support element and said counter element being adjustable.

The adjusting means may further include a through opening in said support element and a threaded opening in said counter element and a movable setscrew fixed in said second member and received in said through opening and extended into the threaded opening. The horizontal relative position of both the support element and counter element is adjusted by adjusting the setscrew whereby the level of the upper side of the second member is adjusted.

The second member may include an insert of elastic dampening material, said insert forming said upper side of said second member and serving the purpose of decreasing or eliminating possible walk noises.

As has been mentioned above elastic bands or strips have been employed in conventional prosthetic hip-joints which were applied at both sides of the hip-joint. The present invention permits one to substantially reduce the size of the joint while maintaining its qualities. Therefore, according to another modification of the invention the second joint member may include a tubular portion in which a tubular part of the artificial leg is to be received, said elastic means being extended into said tubular portion and including a compression spring. The hip-joint may further include a pivot pin having one end pivotally mounted to said first member at a first pivot point and another end pivotally mounted to said second member at a second pivot point.

The compression spring may be operatively connected to said pivot pin so that said first pivot point is above said second pivot point when the joint is in said first position and below said second pivot point when the joint is in said second position. Thereby the necessary elastic means do not require an additional space since they are substantially located in the tubular portion of the second member utilized for receiving the end of the artificial leg. The compression spring may be prestressed and its prestressing may be adjusted. Thus there is no need for the replacement of worn elastic bands as has been the case with conventional hip-joints.

Furthermore, the second joint member may move in its pivoting over an angle of more than 90°, said compression spring applying a maximal counter force to said second member when the latter is moved over an angle of 90° from said first (standing) position. Therefore, the hip-joint according to the invention ensures that the spring force applied to the second member increases over a certain pivoting area and decreases when that certain pivoting area is exceeded. This area is preferably defined by an angle of 90°. If the hip-joint travels over 90° the spring acts on the joint such that a further movement of the joint into the second (sitting) position is significantly facilitated.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 1 is a sectional view of the prothetic hip-joint of the artificial leg of the invention, in a standing position;

FIG. 3 is a sectional view on line III—III of FIG. 1;

FIG. 4 is a partical front view of the prosthetic hip-joint of FIG. 1, for a frontal adjustment;

DETAILED DESCRIPTION OF THE PREFERRED EMBODIMENTS

Figure 2:
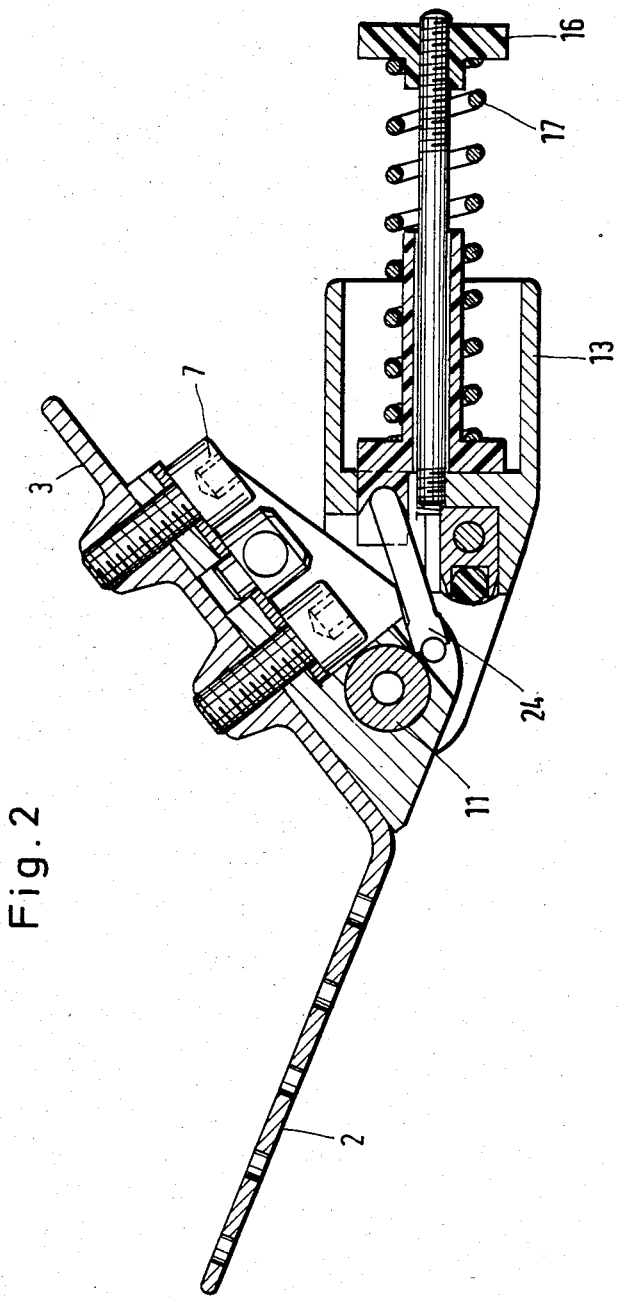
FIG. 2 is a sectional view similar to FIG. 1 but in a sitting position of the artificial leg.

Referring now to the drawings, and first to FIGS. 1 and 2, a prothetic hip-joint includes a fastening angle 1 which has a substantially horizontal shank 2 and a substantially upright shank 3 extended to the shank 2 at an obtuse angle. Horizontal shank 2 has five through openings 4 which receive screws for application of a mounting part 5 (FIGS. 5-7) in the known manner. Rivets or laminated fiber pins of hardenable plastics can be utilized in place of fastening screws.

The prothetic hip-joint of the invention includes a first joint element 6 and a second joint element 10. Joint element 6 is screwed to shank 3 of the fastening angle 1 with two bolts 7. Joint element 6 is formed with two holes 8 vertically spaced from each other and receiving bolts 7 therethrough. The upper hole 8 is formed as a circular oblong opening as clearly shown in FIG. 4. Behind holes 8 is located a lower plate 9.

The second joint element 6 is pivotally supported in the plane of the drawings on the first joint element 6 by means of a hinge joint 11. Two ends of the fork-like portion 12 of joint element 10 embrace joint element 6 at the lateral sides thereof. Second joint element 10 is formed at its free lower end as a hollow tube 13. Centrally of the hollow tube 13 is positioned an axle or shaft 14 which is provided with an outer thread 15 at the lower end thereof. An adjusting nut or disk 16 is screwed on the thread 15 of shaft 14. A compression spring 17 is supported at disc 16 at its one end whereas its second end abuts against a stop disk or washer 18 of a sleeve 19 slidable on the shaft 14. Sleeve 19 is arranged inside of the compression spring 17.

The stop washer 18 in the standing position of the artificial leg bears against a base 20 of the hollow tube 13. Base 20 of tube 13 is formed with an opening 21 through which an extension 22 outwardly projected from the stop washer 18 extends in the upward direction. Extension 22 is formed as a fork-like member and has a receiving depression 23 in which a convex end surface of a pin 24 is supported. Another end of pin 24 which has a shape of a pawl engages a bearing pin 25 which is mounted in joint element 6 and extends parallel to the hinge joint 11. Pin 24 is therefore pivotally supported in the depression 23 of second joint element 10 and is able to pivot about the bearing pin 25.

When the hip-joint is bent forwardly from the standing position shown in FIG. 1 pin 24 will be pressed against the receiving surface of depression 23 whereby sleeve 19 will be urged in the downward direction against the force of compression spring 17. The counter force exerted against the bending movement of the hip-joint will cause a further compression of spring 17 unless pin 24 and sleeve 19 take a position in which they are approximately parallel to each other. In other words, the bending movement through approximately 90° must be accomplished to move the artificial leg from the standing position of FIG. 1. If the hip-joint further bends sleeve 19 will again move upwardly and spring 17 will assist in this further bending movement of the joint unless the hip-joint takes a sitting position shown in FIG. 2.

As seen in FIGS. 1 and 2 the lower edge 26 of the joint element 6 as well as the upper surface of the rear edge 27 of the joint element 10 is inclined whereby these edges do not extend downwardly along the imaginary extension line projected substantially in the direction of elongation of horizontal shank 2 (as shown in FIG. 2).

Second joint element 10 as seen in FIG. 1 bears against the upper face of lower edge 26 of first joint element 6 when the hip-joint is in its standing position. In order to prevent disturbing walk noises from occurring the prothetic hip-joint is provided with an insert 28 the upper side of which is formed of elastic dampening material. In order to adjust insert 28 at the height of the joint there is provided a wedge-like support element 29 which has a sloped surface which bears against the sloped surface of another wedge-like counter element 30 as shown in FIG. 3. A setscrew 32 is fixed in the housing 31 of second element 10. An opening 33 is formed in the wedge-like element 29 which receives the setscrew 32 which is further screwed into a threaded opening 34 formed in the counter wedge-like element 30 whereby elements 29 and 30 cooperate with each other. Upon tightening of setscrew 32 is wedge-like counter element 30 moved towards the right in the plane of the drawing as seen in FIG. 3 so that wedge-like support element 29 will move outwardly as shown by a dashed line *

* The insert 28 itself is not shown in FIG. 3 for the sake of clarity.

When the prothetic hip-joint is in the sitting position the surface 35 of the fork-like portion 12 of joint element 10 bears against the substantially vertically extended edge of the first joint element 6. This stop position needs no adjustment.

Figure 6:
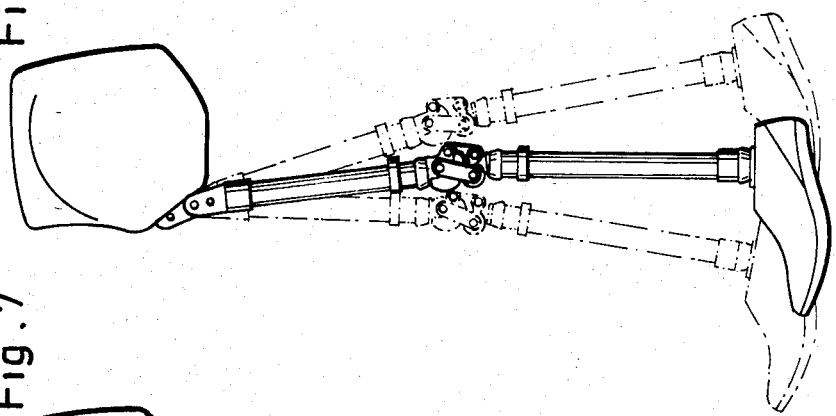
FIG. 6 is a side view of the artificial leg illustrating adjustment possibilities in the frontal plane.
Figure 5:
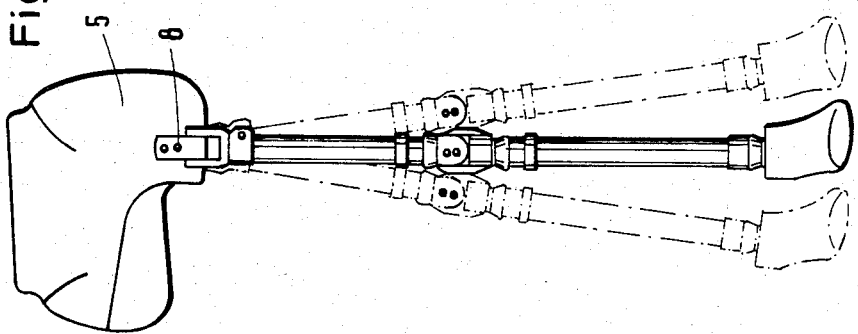
FIG. 5 is a front view of the artificial leg illustrating an adjustment region in the saggital plane.

Reference is now made to FIGS. 5 and 6 which illustrate adjustment possibility of the hip-joint according to the invention in the saggital plane and frontal plane. The adjustment of the hip-joint in the saggital plane is made with the aid of a screw 36 shown in FIG. 1 when screws 7 are loosened and lengthwise opening 8 is released. The adjustment in the frontal plane is carried out with the aid of the above described support element 29.

Figure 7:
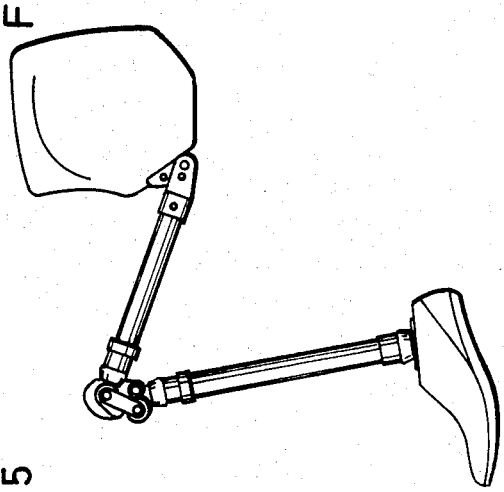
FIG. 7 is a side view of the artificial leg in the sitting position.

FIG. 7 shows that the hip-joint according to the invention in the sitting position does not tend to move in the downward direction so that a user of the artificial leg is not disturbed by the hip-joint when he or she is in the sitting position.

It will be understood that each of the elements described above, or two or more together, may also find a useful application in other types of prothetic hip-joints for artificial legs differing from the types described above.

While the invention has been illustrated and described as embodied in a hip-joint for an artificial leg, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. An articulated hip-joint for an artificial leg, comprising a fastening angle including a substantially horizontal shank and a substantially upright shank extended at an obtuse angle to said horizontal shank; a first joint member connected to said upright shank; a second joint member connectable to the artificial leg and pivotally connected to said first joint member by a pivot so that said second member can be pivoted relative to said first member about said pivot between a first position corresponding to the standing position of the leg and a second position corresponding to the sitting position of the leg; stop surface means on said first member and said second member for limiting the pivoting movement of said second member relative to said first member; and elastic means on said second member for generating an elastic counter force applied to said second member when it is pivoted from said first position into said second position and vice versa so that said first joint member and said second joint member do not extend downwardly over an imaginary extension line drawn from said substantially horizontal shank, when the joint is in said second position.

2. The hip-joint as defined in claim 1, including means for connecting said first member to said upright shank operated so that said first member is pivotable at a small angle relative to said upright shank in a vertical direction.

3. The hip-joint as defined in claim 2, wherein said connecting means include two openings formed in said first member in spaced relationship from each other and two fastening screws extended through said openings, respectively and received in said upright shank, one of said openings being a circular oblong opening.

4. The hip-joint as defined in claim 3, wherein said stop surface means include a lower side of said first member and an upper side of said second member, said upper side pressing against said lower side when the joint is in said first position.

5. The hip-joint as defined in claim 4, further including means for adjusting the position of said upper side at the height thereof.

6. The hip-joint as defined in claim 5, wherein said adjusting means include a wedge-like support element having a sloped surface and a wedge-like counter element having an inclined surface, said sloped surface being supported on said inclined surface, the relative position of said support element and said counter element being adjustable.

7. The hip-joint as defined in claim 6, wherein said adjusting means further include a through opening in said support element and a threaded opening in said counter element and a movable setscrew fixed in said second member and received in said through opening and extended into said threaded opening.

8. The hip-joint as defined in claim 7, wherein said second member has an insert of elastic dampening material, said insert forming said upper side of said second member.

9. The hip-joint as defined in claim 8, wherein said second member includes a tubular portion in which a tubular part of the artificial leg is to be received, said elastic means being extended into said tubular portion and including a compression spring.

10. The hip-joint as defined in claim 9, further including a pivot pin having one end pivotally mounted to said first member at a first pivot point and another end pivotally mounted to said second member at a second pivot point.

11. The hip-joint as defined in claim 10, wherein said compression spring is operatively connected to said pivot pin so that said first pivot point is above said second pivot point when the joint is in said first position and below said second pivot point when the joint is in said second position.

12. The hip-joint as defined in claim 11, wherein said second member in said pivoting movement moves over an angle of more than 90°, said compression spring applying a maximal counter force to said second member when the latter is moved over 90° from said first position.

13. The hip-joint as defined in claim 12, wherein said compression spring is prestressed and its prestressing is adjustable.

* * * * *